United States Patent [19]
Vara et al.

[11] Patent Number: 4,919,692
[45] Date of Patent: Apr. 24, 1990

[54] PROCESS FOR REMOVING SOLVENTS AND OTHER CONTAMINANTS FROM AN INLET SOLVENT LADEN AIR PATH

[75] Inventors: Tomas E. Vara; Clyde Anderson, both of Vero Beach, Fla.

[73] Assignee: Vara International, Inc., Vero Beach, Fla.

[21] Appl. No.: 286,655

[22] Filed: Dec. 19, 1988

[51] Int. Cl.⁵ .............................................. B01D 53/04
[52] U.S. Cl. ............................................ 55/59; 55/74
[58] Field of Search .............................. 55/59, 62, 74

[56] References Cited
U.S. PATENT DOCUMENTS

| | | |
|---|---|---|
| 2,760,594 | 8/1956 | Browning et al. |
| 3,343,916 | 9/1967 | Cahn et al. |
| 3,883,325 | 5/1975 | Fuhring et al. |
| 3,963,401 | 6/1976 | Stockford et al. |
| 4,018,704 | 4/1977 | Kurango. |
| 4,056,369 | 11/1977 | Quackenbush. |
| 4,219,537 | 8/1980 | Steiner. |
| 4,261,716 | 4/1981 | Schwartz et al. |
| 4,276,058 | 6/1981 | Dinsmore. |
| 4,286,972 | 9/1981 | Savage et al. |
| 4,289,505 | 9/1981 | Hardison et al. ........................ 55/59 |
| 4,331,456 | 5/1982 | Schwartz et al. |
| 4,343,629 | 8/1982 | Dinsmore et al. |
| 4,414,003 | 11/1983 | Blaudszun. |
| 4,487,614 | 12/1984 | Yon. |
| 4,553,983 | 11/1985 | Baker. |
| 4,596,587 | 6/1986 | Litzenburger et al. ................. 55/59 |
| 4,661,256 | 4/1987 | Johnson. |
| 4,689,054 | 8/1987 | Vara et al. |

FOREIGN PATENT DOCUMENTS 2703737  8/1978  Fed. Rep. of Germany .......... 55/59

OTHER PUBLICATIONS

Operations Improvements, by M. S. Thomas, Exec V. P., Vara, Int'l, "Focus on Solvent Recovery".
"Spontaneous Combustion of Carbon Beds" by: A. A. Navjokos, Eastman Kodak, Rochester, N.Y.
"Vapor-Phase Adsorption Cuts Pollution, Recovers Solvents", by: C. S. Parmele; W. L. O'Connell; H. S. Basdekis of Hydroscience, Inc.
Special Report: Volatile Organic Compounds by: Paul N. Cheremisinoff.
Solvent Recovery System Controls Pollution While Saving Money (flyer by Vara Int'l).
Solvent Recovery-Answer to Efficient Pollution Control in Production of Pressure-Sensitive Materials (flyer by Vara, Int'l).

Primary Examiner—Charles Hart
Attorney, Agent, or Firm—Steele, Gould & Fried

[57] ABSTRACT

A process is provided for the removal of solvents and other contaminants from an inlet solvent laden air (SLA) path. The process comprises the step of passing the SLA through an adsorbent in an adsorber. The adsorbent is regenerated when it becomes saturated with solvents. The regeneration step is performed by passing a regenerating fluid, preferably steam, through the adsorber. The steam removes solvents from the adsorbent and transports the solvents out of the adsorber. The steam and solvents are condensed in a condensation step. Water is separated from the condensaton produced in a separation step such as decantation and distillation. The condensed water is passed to a steam generation step. The recovered water is used as boiler feed water to generate low pressure steam. The steam generated in the steam generation step is recycled to the adsorbent regeneration step. The recycling of the water used for regenerating the adsorbent eliminates a waste water stream, thereby eliminating or reducing waste water treatments.

3 Claims, 2 Drawing Sheets

PROCESS FOR REMOVING SOLVENTS AND OTHER CONTAMINANTS FROM AN INLET SOLVENT LADEN AIR PATH

BACKGROUND OF THE INVENTION

1. Field of the Invention

This invention relates generally to air purification processes, and more particularly to processes for regenerating adsorbents used in the removal of solvents and other contaminants from solvent laden air (SLA) streams.

2. Description of the Prior Art

Solvents are commonly removed from a SLA stream through contact with an adsorbent such as activated carbon. When the adsorbent becomes saturated or nearly saturated with solvent, the adsorbent is regenerated using steam to heat up the adsorbent and displace the solvents. The steam and solvents leave the adsorber and are condensed. Two layers form if the solvents are insoluble in water. In this case, the solvents may be separated from the water by decantation. If the solvents are soluble in water, there will not be any separation, and the solvents must be separated from water by other means such as distillation.

Prior art regeneration processes require that the water layer from decantation be further treated by air stripping or steam stripping to remove the solvents which remain in the water layer before the water is discharged to the sewer. Government standards require the removal of solvents from these effluent water streams prior to sewering these streams. The removal of solvents from water exiting regeneration processes is expensive. Treatment is particularly expensive when the solvents are soluble in water.

SUMMARY OF THE INVENTION

It is an object of the invention to eliminate the waste water stream in the regeneration portion of solvent recovery processes.

It is another object of the invention to provide a process for the recovery of solvents and other contaminants from SLA streams which is environmentally safe.

These and other objects are accomplished by a process for regenerating an adsorbent used to remove solvents and other contaminants from an inlet SLA stream in which the waste water stream is minimized, and preferably substantially eliminated. The regeneration includes the steps of:

(i) passing steam through the adsorber to desorb contaminants from the adsorbent;

(ii) condensing the steam and solvents exiting the adsorber to produce a condensate;

(iii) separating the condensate into a solvent rich fraction and a water layer fraction;

(iv) generating steam from the water fraction; and, (v) recycling the steam of step (iv) to the desorption step (i).

The separation step (iii) is preferably selected from decantation or distillation. Insoluble solvents readily separate from water in two or more layers, depending on their density. These solvents can usually be separated from the water by decantation. It is not necessary that the water be completely free of solvent to be used as the source of boiler feed water for generating steam in a low pressure boiler. Therefore, in the case of highly insoluble solvents such as toluene, hexane, and heptane, the water layer from the decantation step may be used directly as boiler feed water.

Solvents which are miscible in water cannot be efficiently separated by decantation. These solvents, such as ethanol, propanol, and tetrahydrofuran, must be separated from the water by suitable separation processes such as distillation. The water from the distillation column bottoms may be recycled to the steam regenerator. The water leaving the base of the column does not have to be free of solvent to be used for generating low pressure steam, and the required purity is significantly less than would be required to meet environmental standards for sewering the water, which might be in the parts-per-billion (PPB) range.

Initial steam passed through the adsorber is condensed as the adsorbent heats. This condensate is preferably recycled to the steam generation step (iv). All of the vapor exiting the adsorber is not condensed in the condensation step (ii). The gases which exit the condenser are preferably recycled to an adsorber for further contact with the adsorbent.

BRIEF DESCRIPTION OF THE DRAWINGS

There are shown in the drawings embodiments which are presently preferred it being understood, however, that the invention is not limited to the precise arrangements and instrumentalities shown, wherein.

DETAILED DESCRIPTION OF THE PREFERRED EMBODIMENTS

Figure 1:
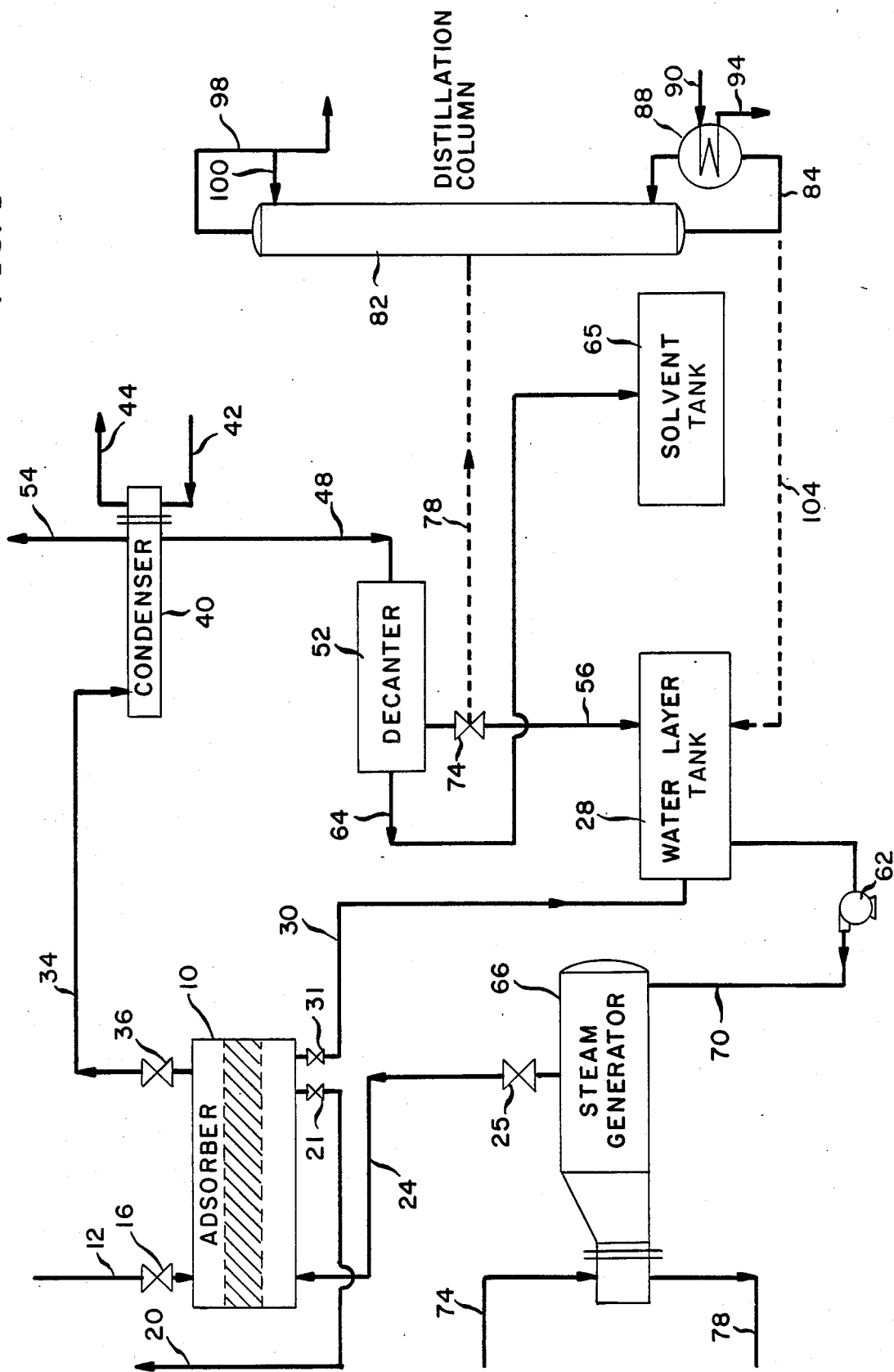
FIG. 1 is a schematic diagram of a first embodiment of the invention.

The process of the invention provides for the removal of solvents from an inlet solvent laden air (SLA) path utilizing an adsorbent. There is shown schematically in FIG. 1 a preferred process according to the invention. The SLA enters an adsorber 10 through a SLA inlet path 12. The flow of inlet SLA is controlled by an SLA inlet valve 16. The SLA is passed through an adsorbent, preferably a bed of activated carbon. Solvents in the air stream are adsorbed by the adsorbent. Purified air leaves the adsorber 10 through an air exit path 20 controlled by a valve 21 and can usually be vented.

When the adsorbent becomes saturated with solvents, the adsorbent is regenerated. The adsorbent is preferably regenerated when desorption equilibrium is attained or nearly attained, or when environmental limits of solvent particles are reached in the air leaving the adsorber.

The process of the invention preferably provides for essentially closed loop regeneration of the adsorbent. The regenerating gas, steam, is passed to the adsorber 10 through a steam inlet path 24 controlled by a valve 25 to strip solvents from the adsorbent. Steam condenses as the adsorbent heats, and the adsorber condensate is transported to a water tank 28 through an adsorber condensate exit 30 controlled by a valve 31. The steam and solvent vapors are transported from the adsorber 10 by an adsorber steam exit path 34, which is controlled by a steam exit valve 36. The steam and solvent vapors exiting the adsorber are preferably between 200 degrees F. and about 230 degrees F.

The steam and solvent vapors exiting the adsorber 10 are passed to a condenser 40. The condenser 40 is supplied with cooling means such as water which enters the condenser by a condensor water inlet path 42 and exits the condenser by a condensor water outlet path 44. The temperature of the cooling water that is required depends on process parameters, and particularly on the solvents being condensed. Condensed water and solvents exit the bottom of the condenser through a condenser liquid exit path 48 and are transported to a decanter 52. Non-condensibles leave the condenser 40 through a condenser vapor exit path 54, which preferably returns the non-condensibles to another adsorber for adsorption. The temperature of the fluids leaving the condenser 40 will depend on the particular solvents being removed and other process parameters.

The decanter 52 separates the liquid product from the condenser into a solvent rich fraction and a water layer fraction. The water layer fraction may, for example, form at the bottom of the decanter 52 and exit through a heavy fraction exit path 56 to the water storage tank 28. The solvent rich fraction, which forms at the top of the decanter 52, leaves the top of the decanter 52 through a decanter light fraction exit path 64 and is passed to a solvent tank 65.

The solvent tank 65 receives the solvent rich fraction from the path 64. It is desirable that the solvents from this fraction be processed and reused, if possible. Otherwise, these products must be disposed by suitable processes and according to acceptable standards.

The water layer fraction which, in this embodiment, leaves the bottom of the decanter 52, may be sufficiently free of solvent that it may be used directly for further steam generation. Where solvents that are miscible with water are encountered, however, it may be necessary to further process this stream to reduce the concentration of these contaminants to acceptable levels.

The dashed lines in FIG. 1 indicate the exit and return paths to one such further separation process, in this embodiment, distillation. A control valve 74 can be utilized to direct the flow of the water layer fraction from the heavy fraction exit path 56 to a distillation inlet path 78. The bottoms of the distillation column 82 are heated by a circulation path 84. A heat exchanger 88 heats the bottoms circulated through the path 84. The heat exchanger 88 can receive heat through a steam inlet path 90, which steam exits through a steam outlet path 94. The solvent product from the distillation will normally exit the top of the distillation column 82, as through a solvent exit path 98. A portion of the solvent exiting through the path 98 can be returned to the column 82 through a return line 100. A portion of the substantially contaminant free regenerating fluid (here water) in the recirculation path 84 is passed to the water storage tank 28 through a distillation column water outlet path 104.

The concentrations in the different vapor and liquid phases will be determined, at the limit, by equilibrium conditions for the compounds that are present and operating parameters such as temperature and inlet concentrations. The equilibrium condition will be disrupted by the constant withdrawal of compounds from the process. A dynamic equilibrium may be attained, but must be calculated or determined empirically on a case by case basis. Data of solubilities for many binary and ternary systems is available in the literature. Data for complex mixtures must be established in the laboratory.

The water layer tank 28 is a holding tank for the water. The water is pumped by a pump means 62 as needed to a steam generator 66 through a steam generator inlet path 70.

The steam is generated by heat which may be provided by electricity, high pressure steam, or the combustion of a fuel. A high pressure steam enters the steam generator 66 through a high pressure steam inlet path 74 and exits the steam generator 66 through a high pressure steam exit path 78. The high pressure steam is preferably at least 40 PSIG and condenses on the tube side of the steam generator. Steam leaving the steam generator 66 is transported by the steam inlet path 24 to the adsorber 10 to regenerate the adsorbent.

Where the bulk of the solvents and contaminants in the process stream are miscible with water, decantation will normally be inappropriate. Solvents such as ethanol, propanol, tetrahydrofuran and others, which are miscible in water, do not separate into two phases. These solvents will not separate by decantation and must be separated by another process.

Figure 2:
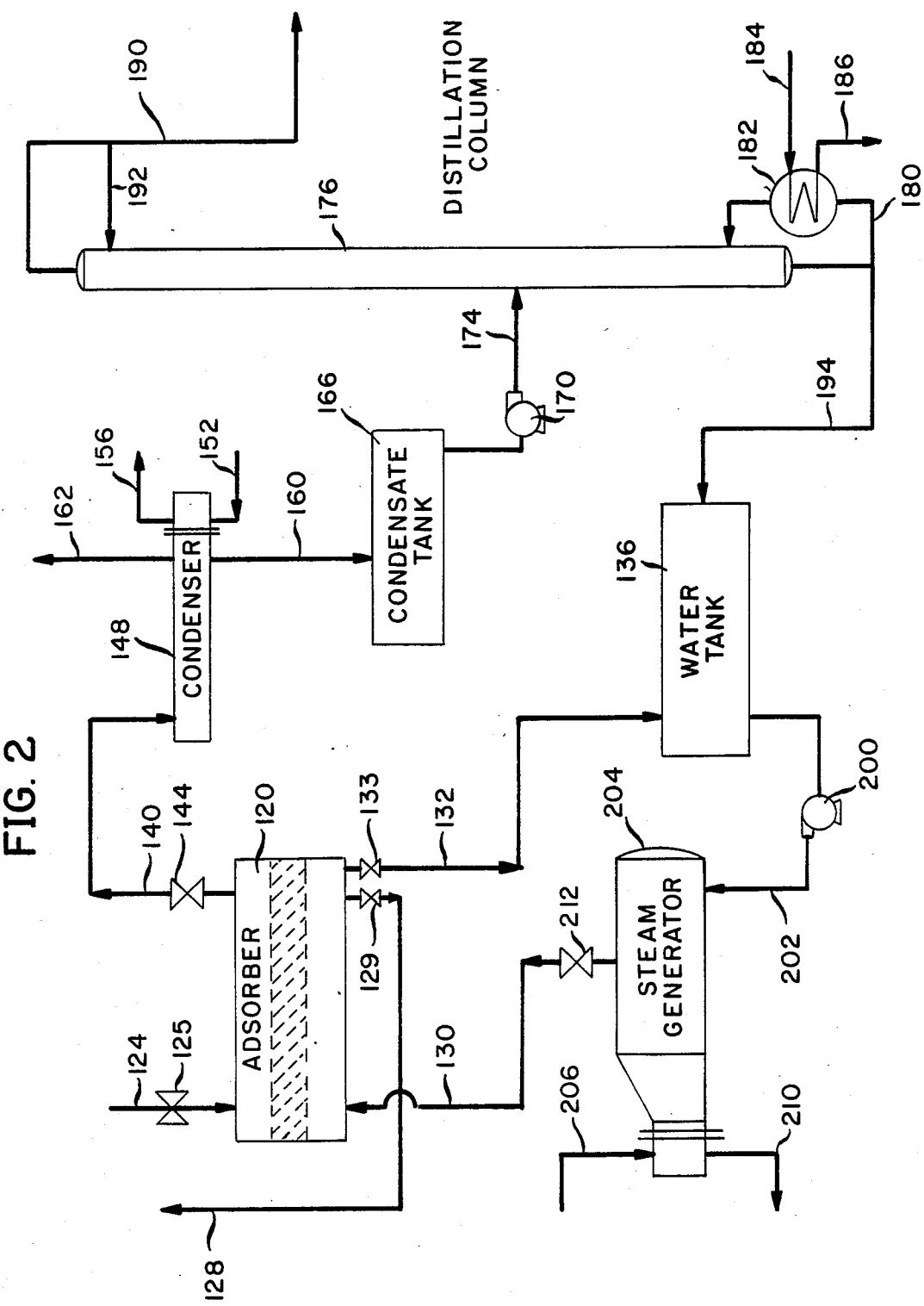
FIG. 2 is a schematic diagram of a second embodiment of the invention.

FIG. 2 illustrates another embodiment of the invention wherein the condensation product is separated by distillation. An adsorber 120 receives SLA from a SLA inlet path 124 controlled by a valve 125. Purified air exits through the air exit path 128 controlled by a valve 129. The adsorbent is periodically regenerated by a flow of regenerating fluid, preferably steam, which is received from an adsorber steam inlet path 130. Initial steam passed through the adsorbent will condense as the adsorbent heats, and this condensation is passed through an adsorber condensate outlet path 132 controlled by a valve 133 to a water storage tank 136.

Steam and solvents exit the adsorber 120 through an adsorber solvent exit path 140, which flow is controlled by an adsorber solvent exit path valve 144. The steam and solvents are passed to a condenser 148, which can be cooled by suitable means known in the art. The condenser 148 can receive cooling liquid from a cooling liquid inlet path 152. The cooling liquid exits the condenser 148 through a cooling liquid exit path 156. The condensate product leaves the condenser 148 through a condensate exit path 160. Non-condensibles leave the condenser 148 through a non-condensibles condenser exit path 162, which preferably returns the non-condensibles to the another adsorber for readsorption. The condensate leaving the condenser 148 is passed to a condensate storage tank 166. A pump 170 can be used to transport condensate from the condensate tank 166 through a distillation column inlet path 174 to a distillation column 176.

The distillation column 176 is adapted to separate the miscible solvents from the regenerating fluid, here water. The bottoms of the distillation column 176 are recirculated through a recirculation path 180. A heat exchanger 182 heats the bottoms flowing through the recirculation path 180. The heat exchanger 182 receives heat from suitable means, such as the steam inlet path 184, which steam exits the heat exchanger 182 through a steam exit path 186. The solvents will normally exit the top of the column through a solvent exit path 190. A portion of the exiting solvents are returned to the column 176 through a reflux path 192. A portion of the bottoms is withdrawn through a distillation column product outlet path 194 and is passed to the water storage tank 136.

Water in the storage tank 136 can be pumped by a pump 200 through a steam generator inlet path 202 to the steam generator 204. The steam generator 204 can be heated by suitable means known in the art such as high pressure steam, which can enter the steam generator 204 through a high pressure steam inlet path 206, and which can exit through a high pressure steam outlet path 210. Steam generated in the steam generator 204 exits through the adsorber steam inlet path 130. Flow through the adsorber steam inlet path 130 is controlled by a control valve 212.

Should the contaminants form azeotropes with water, further processing may be required to dehydrate the solvents. The pH of the water can be neutralized, as needed, in the water tank 136.

EXAMPLE 1

Toluene used in a coating operation must be separated from an air stream before the air stream can be vented to the atmosphere. A toluene laden air path is passed through an adsorbent wherein the toluene is adsorbed on the adsorbent. The adsorbent is regenerated when needed by passing steam through the adsorbent.

The toluene and steam vapor exiting the adsorber are condensed. The condensate is transported to a decanter for separation. In the decanter two phases form wherein the lighter, top layer contains most of the toluene and the lower, heavier layer contains mostly water. The light fraction leaving the top of the decanter and containing the toluene is transported to a storage tank. The solubility of water in toluene is slight, on the order of about 500 ppm, and the toluene product may therefore be reused in most applications without further processing.

The water layer leaving the decanter contains about 600 ppm of toluene, and usually cannot be released without further treatment. The water is therefore passed to a water layer tank and is then used to generate steam for further regeneration. High pressure steam at about 40 PSIG is used to vaporize this water in the steam generator. The steam generated in the steam generator and passed to the adsorbers is at about 20 PSIG.

EXAMPLE 2

Solvents such as ethanol, propanol, tetrahydrofuran and other solvents which are miscible in water do not separate into two or more layers and these solvents must be separated from water by distillation.

Solvent laden air (SLA) is passed through the adsorbent bed where the solvents are adsorbed on the carbon. The solvents are then desorbed using steam. The solvents and steam are condensed and flow to the condensate tank. The homogenous mixture of solvent and water is pumped to the distillation column where the solvents are concentrated and removed overhead from the column. The water is removed from the base of the column and flows to a water holding tank where it is treated and filtered before recycling to the steam generator. As in the case of Example 1, the water used in this system is recovered and recycled so that there is no waste water to sewer.

There are also other combinations of solvents having varying degrees of solubilities in water. In such cases it may be necesary to distill the water layer from decantation to remove some solvent which remains in the water layer before the water can be recycled to steam generator.

The process of the invention can be utilized to remove a number of solvents in different proportions from the SLA path. Although steam is a preferred regenerating fluid, the principles disclosed herein could apply to other regenerating fluids. Particular selection, sizing and precise layout of the process equipment must, of course, depend upon the operation parameters and conditions. The number, type, dimension and design of the adsorbers, decanters, pumps, columns, tanks, exchangers, condensers, and generators, for example, can vary. These process characteristics must be selected according to known process design principles. Accordingly, this invention may be embodied in other specific forms without departing from the spirit or essential attributes thereof, and reference should therefore be made to the following claims, rather than the foregoing specification, as indicating the scope thereof.

I claim:

1. A process for regenerating adsorbents used to remove solvents from an inlet solvent laden air (SLA) path, said solvents being at least partially miscible in water, comprising the steps of:
   (i) passing steam through the adsorbent to desorb solvents from the adsorbent;
   (ii) condensing the steam and solvents leaving the adsorbent to produce a condensate;
   (iii) distilling the condensate into at least one solvent-rich fraction and a water fraction;
   (iv) generating steam from the water fraction of the distillation step (iii); and,
   (v) recycling the steam of step (iv) to the desorption step (i).

2. The process of claim 1, wherein condensate leaving said condensation step (ii) is separated by decantation into a solvent-rich fraction and a water fraction, said decantation water fraction being passed to said distillation step (iii).

3. The process of claim 1, wherein steam condensed in the desorption step (i) is passed to the steam generation step (iv).

* * * * *